(12) United States Patent
Tasaki

(10) Patent No.: US 7,787,587 B2
(45) Date of Patent: Aug. 31, 2010

(54) IMAGE RADIOGRAPHING SYSTEM

(75) Inventor: Misae Tasaki, Hino (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 33 days.

(21) Appl. No.: 11/859,392

(22) Filed: Sep. 21, 2007

(65) Prior Publication Data

US 2008/0075228 A1 Mar. 27, 2008

(30) Foreign Application Priority Data

Sep. 26, 2006 (JP) .............................. 2006-260981

(51) Int. Cl.
*A61B 6/00* (2006.01)
*H05G 1/42* (2006.01)
*H05G 1/64* (2006.01)

(52) U.S. Cl. ..................... 378/37; 378/98.7; 378/108

(58) Field of Classification Search ................. 378/37, 378/97, 98.7, 108; 382/132
See application file for complete search history.

(56) References Cited

U.S. PATENT DOCUMENTS

| | | | | |
|---|---|---|---|---|
| 6,556,655 B1 * | 4/2003 | Chichereau et al. | ......... | 378/108 |
| 7,031,429 B2 * | 4/2006 | Akagi | ......................... | 378/37 |
| 7,039,155 B2 * | 5/2006 | Akagi | ......................... | 378/37 |
| 7,209,543 B2 * | 4/2007 | Strommer | ..................... | 378/97 |
| 7,319,735 B2 * | 1/2008 | Defreitas et al. | ............. | 378/37 |
| 7,400,707 B2 * | 7/2008 | Nakayama et al. | .......... | 378/108 |
| 7,431,500 B2 * | 10/2008 | Deych et al. | ................. | 378/207 |
| 7,433,445 B2 * | 10/2008 | Okada et al. | .................. | 378/97 |
| 7,443,949 B2 * | 10/2008 | Defreitas et al. | ............. | 378/37 |
| 7,443,950 B2 * | 10/2008 | Sendai | ......................... | 378/37 |
| 7,453,979 B2 * | 11/2008 | Sendai | ......................... | 378/23 |
| 7,561,667 B2 * | 7/2009 | Nakayama | .................... | 378/97 |
| 2001/0019600 A1 * | 9/2001 | Sklebitz | ..................... | 378/108 |
| 2009/0118614 A1 * | 5/2009 | Sendai | ........................ | 600/437 |

\* cited by examiner

*Primary Examiner*—Allen C. Ho
(74) *Attorney, Agent, or Firm*—Finnegan, Henderson, Farabow, Garrett & Dunner, L.L.P.

(57) ABSTRACT

A radiographing apparatus of an image radiographing system is equipped with plural sensors each detecting an amount of radiation transmitted through a breast in the course of radiographing, and it transmits sensor data showing an output value of each sensor to a control apparatus through a network. In the control apparatus, a mammary gland content rate corresponding to an output value of each sensor is acquired based on sensor data transmitted from the radiographing apparatus, then, a breast type is discriminated based on an average mammary gland content rate and on the state of distribution of mammary gland content rates, and image processing conditions are established based on the results of discrimination of the breast type. Then, based on the image processing conditions thus established, image processing is given to image data acquired from a reading apparatus.

19 Claims, 13 Drawing Sheets

HOME POSITION
(ROTATION ANGLE 0°)

DETECTION
ANGLE (−) 30°

HOME POSITION
(ROTATION ANGLE 0°)

DETECTION
ANGLE (+) 30°

FIG. 8

| | | | | RADIOGRAPHING ORDER INFORMATION 3510 | | | | | | RADIOGRAPHING PERFORMANCE INFORMATION 3515 | | |
|---|---|---|---|---|---|---|---|---|---|---|---|---|
| | PATIENT INFORMATION 3512 | | | | RADIOGRAPHING INFORMATION 3513 | | | | | | | |
| ORDER ID 3511 | PATIENT ID | NAME | AGE | ... | RADIOGRAPHING REGION AND DIRECTION | RADIOGRAPHING DATE | ... | CASSETTE ID 3514 | RADIOGRAPHING REGION AND DIRECTION | TUBE VOLTAGE (kV) | COMPRESSING PRESSURE (mm) | SENSOR OUTPUT VALUE |
| 0001 | 1001 | HANAKO YAMADA | 40 | ... | LEFT OBLIQUE | 2003/4/1 | ... | 1010101 | | | | ... |
| 0002 | 1001 | HANAKO YAMADA | 40 | ... | RIGHT OBLIQUE | 2003/4/1 | ... | 1010102 | RIGHT OBLIQUE | 60 | 10 | ... |
| 0003 | 1001 | HANAKO YAMADA | 40 | ... | LEFT VERTICAL | 2003/4/1 | ... | 1010103 | | | | ... |
| 0004 | 1001 | HANAKO YAMADA | 40 | ... | RIGHT VERTICAL | 2003/4/1 | ... | 1010104 | | | | ... |
| 0005 | 2050 | KYOKO SUZUKI | 50 | ... | LEFT OBLIQUE | 2003/4/1 | ... | | | | | ... |
| ... | ... | ... | ... | ... | ... | ... | ... | ... | ... | ... | ... | ... |

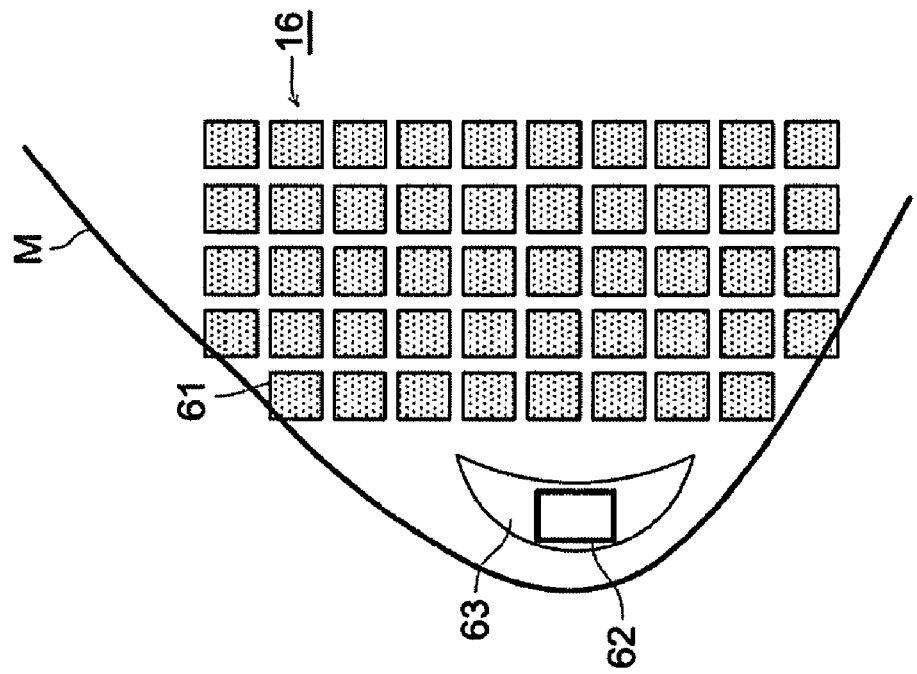
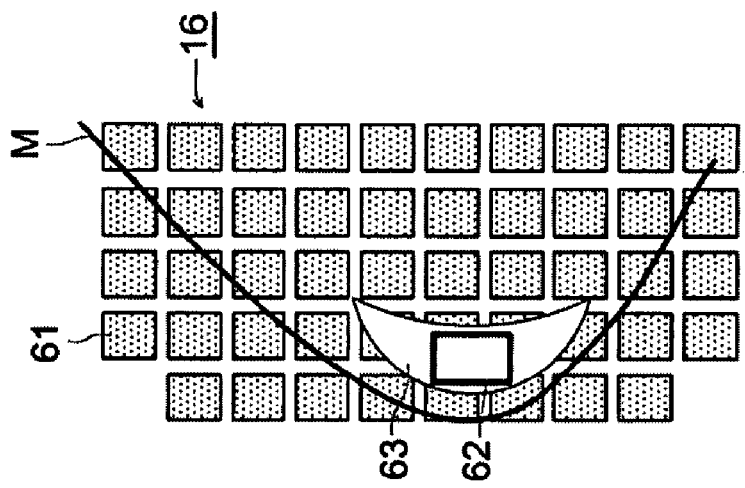

FIG. 12 (a)

| 60 | 60 | 70 | 70 | 70 | 70 | 70 | 70 | 60 | 60 |
| 70 | 70 | 80 | 80 | 80 | 80 | 80 | 80 | 70 | 70 |
| 0  | 80 | 80 | 80 | 80 | 80 | 80 | 80 | 80 | 0  |
| 0  | 0  | 80 | 80 | 80 | 80 | 80 | 80 | 0  | 0  |
| 0  | 0  | 80 | 80 | 80 | 80 | 0  | 0  |    |    |

AVERAGE MAMMARY GLAND CONTENT RATE : HIGH
MAMMARY GLAND DISTRIBUTION : BROAD
⇒ HIGH DENSITY TYPE

FIG. 12 (b)

| 0 | 0 | 0  | 0  | 0  | 0  | 0  | 0 | 0 | 0 |
| 0 | 0 | 5  | 5  | 5  | 0  | 5  | 0 | 0 | 0 |
| 0 | 5 | 10 | 10 | 10 | 10 | 10 | 5 | 5 | 0 |
| 0 | 0 | 10 | 10 | 10 | 10 | 10 | 10| 0 | 0 |
| 0 | 0 | 40 | 50 | 50 | 40 | 0  | 0 |   |   |

AVERAGE MAMMARY GLAND CONTENT RATE : LOW
MAMMARY GLAND DISTRIBUTION : NARROW
⇒ FATTY TYPE

FIG. 12 (c)

| 5 | 5  | 5  | 5  | 5  | 5  | 5  | 5  | 5  | 5 |
| 5 | 10 | 10 | 10 | 10 | 5  | 10 | 10 | 5  | 5 |
| 0 | 20 | 40 | 20 | 20 | 10 | 50 | 60 | 20 | 0 |
| 0 | 0  | 80 | 40 | 80 | 60 | 80 | 80 | 0  | 0 |
| 0 | 0  | 80 | 80 | 80 | 80 | 0  | 0  |    |   |

OTHERS ⇒ OTHER TYPE

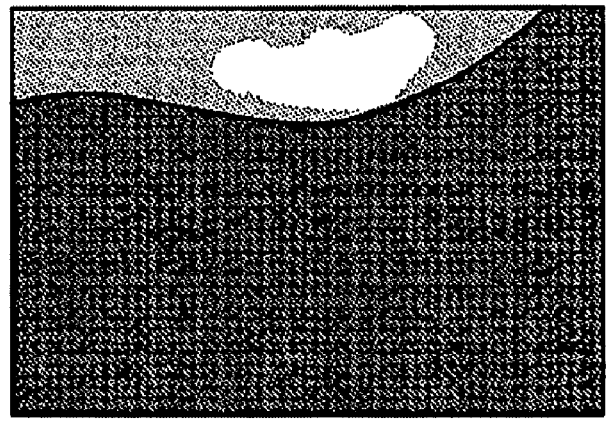
FIG. 13 (c) OTHER TYPE ⇒ CONTRAST: γ = 4.0 FREQUENCY EMPHASIS DEGREE: 3
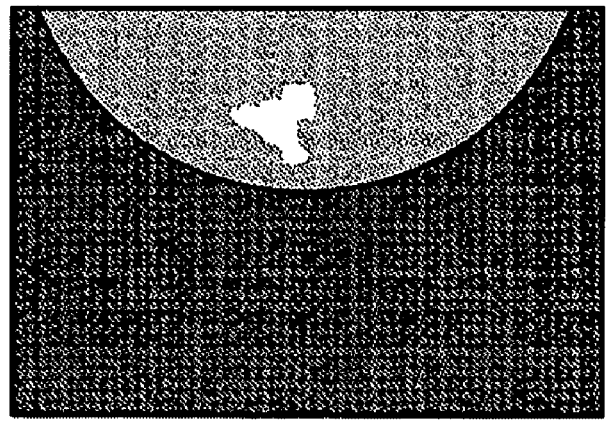
FIG. 13 (b) FATTY TYPE ⇒ CONTRAST: γ = 5.0 FREQUENCY EMPHASIS DEGREE: 4
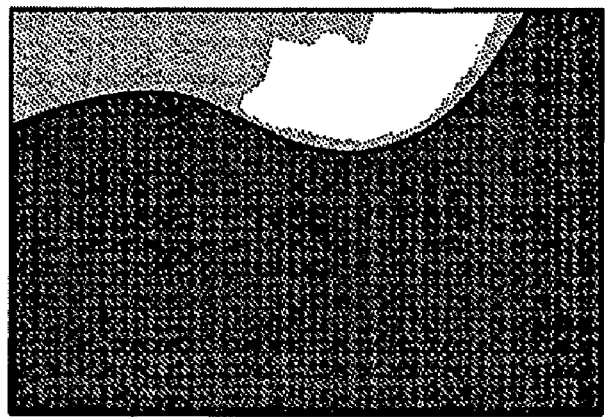
FIG. 13 (a) HIGH DENSITY TYPE ⇒ CONTRAST: γ = 3.0 FREQUENCY EMPHASIS DEGREE: 4

IMAGE RADIOGRAPHING SYSTEM

This application is based on Japanese Patent Application No. 2006-260981 filed on Sep. 26, 2006 in Japanese Patent Office, the entire content of which is hereby incorporated by reference.

BACKGROUND OF THE INVENTION

The present invention relates to an image radiographing system that employs radiation for radiographing.

Medical images obtained through radiographing by the use of radiation have been widely used as an image for diagnoses. It is important to control properly a radiation dose to be irradiated, in radiographing, for avoiding excessive radiation exposure. Further, a radiation dose and image quality are closely related to each other, and if a radiation dose is not proper, graininess of an image is worsened and diagnostic performance is lowered. It is therefore important to control a radiation dose properly, also for securing diagnostic performance of images. Therefore, on a radiographing apparatus that performs radiographing, there is mounted an automatic exposure controller (AEC) so that a radiation dose may be controlled to be appropriate.

The automatic exposure controller is equipped with a sensor to detect a radiation dose transmitted through a subject, and a period of time for radiation irradiation is controlled based on the radiation dose detected by this sensor. When the diagnosing object is a breast, it is important to irradiate radiation in an optimum amount of dose to mammary gland tissue, because most breast cancers are caused from mammary gland tissue. There is proposed a technology to show where the sensor is located on a breast by projecting a sensor position on the breast before irradiation of X-ray, so that the position of the sensor that detects a radiation dose may agree with a portion where the mammary gland density is highest (for example, see Patent Document 1)

However, some of radiation images are hard to read because of characteristics of the images or characteristics of the subject itself. For example, in the case of examination radiographing, mammary gland tissue and fat tissue are intermingled on a breast. Breast images are classified into the following four types of breast (hereinafter referred to as a breast type), depending on a rate of mammary gland tissue within the breast and on the state of distribution of mammary gland tissue.

(1) Fatty Type

This is a type wherein a breast area is almost perfectly replaced by fat. Since a fatty area indicates high density on a film image, and an affected area (cluster of micro-calcifications and a tumor) indicates low density, if the affected area is included in an area of radiographing, it is easy to detect the affected area.

(2) Mammary Gland Scattered Type

This is a type wherein mammary gland substances are scattered in a breast area that is replaced by fat. It is relatively easy to detect an affected area.

(3) Heterogeneous High Density Type

This is a type wherein a plurality of fat tissue are scattered in mammary gland substances, and heterogeneous density is indicated. Since a mammary gland tissue indicates low density on an image compared with fat, there is a possibility that an affected area is veiled by the mammary gland tissue.

(4) High Density Type

Fats are hardly intermingled in mammary gland substances, and a detecting rate for affected areas is low.

In a breast image classified to be high density type among the aforesaid various breast types, sufficient contrast cannot be obtained, because mammary gland tissues are distributed uniformly, and an area of the same density extends in a mammary gland area. Therefore, it has been difficult to discover an affected area such as a microscopic calcified cluster wherein microscopic low density dots are gathered to exist in a mammary gland area. In contrast to this, in another breast type such as the mammary gland scattered type, contrast is easily indicated in a mammary gland area, and it is relatively easy to detect an affected area, because high density fatty areas are intermingled in the mammary gland area.

As stated above, characteristics of images are different from each other depending on the structure of tissues having an individual difference for each subject such as a mammary gland area. Therefore, if the same image processing condition is used for image processing for breast images obtained through radiographing, it is impossible to acquire the optimum image, which has been a problem.

[Patent Document 1] Japanese Patent Publication Open to Public Inspection No. 8-80295

SUMMARY

An objective of the invention is to obtain a stable image processing results even when the structure of tissues of a subject has a large individual difference.

For achieving the aforesaid objective, an embodiment of the invention is an image forming system having therein a radiographing apparatus equipped with a radiographing device that irradiates a radiation on a breast by a radiation source to radiograph a breast, a detecting device that has plural detecting elements and detects a dose of a radiation transmitted through a breast in the course of radiographing, and with a control device that controls the aforesaid radiation source based on output values of the plural detecting elements, and the image forming system further has a control apparatus that conducts image processing on a breast image obtained through radiographing and generates images for diagnoses wherein a discrimination device that discriminates a type of the radiographed breast based on output values of the plural detecting elements and an image processing condition setting device that establishes image processing conditions for the aforesaid image processing based on the results of discrimination conducted by the aforesaid discrimination device are provided.

BRIEF DESCRIPTION OF THE DRAWINGS

FIG. 8 is a diagram showing an example of data construction of order file 351.

FIG. 11(a) shows an example wherein ROI 62 is in effective area 61 of a sensor. FIG. 11(b) shows an example wherein ROI 62 is not in effective area 61 of a sensor.

FIG. 12 shows diagrams for illustrating discrimination methods for breast types based on an average mammary gland content rate and mammary gland content rate distribution.

FIG. 13 is a diagram for illustrating an example of a method of setting image processing conditions corresponding to a breast type.

DETAILED DESCRIPTION OF THE PREFERRED EMBODIMENTS

Figure 1:
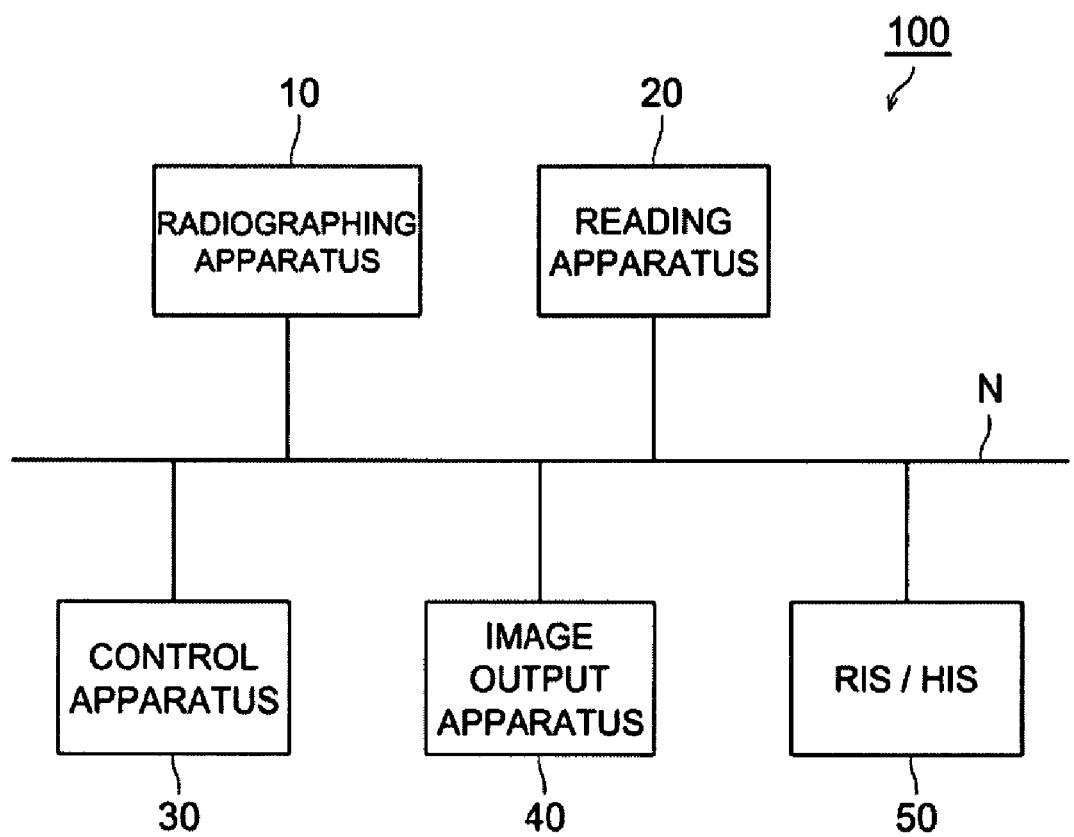
FIG. 1 is a conceptual diagram showing the overall structure of image radiographing system 100 in the present embodiment of the invention.

In the aforesaid image radiographing system, another embodiment of the invention is characterized in that the aforesaid discrimination device acquires a mammary gland content rate for the breast corresponding to each position in the aforesaid plural detection elements based on output values of the plural detection elements, and discriminates a type of the radiographed breast based on the mammary gland content rate and on the state of distribution of the mammary gland content rates.

In the aforesaid image radiographing system, still another embodiment of the invention is characterized in that the aforesaid radiographing apparatus is equipped with a transmission device that transmits output values of the aforesaid plural detection elements to the aforesaid control apparatus, and aforesaid discrimination device and image processing condition setting device are provided on the control apparatus.

In the aforesaid image radiographing system, still more another embodiment of the invention is characterized in that the aforesaid discrimination device is equipped on the aforesaid radiographing apparatus, and the aforesaid image processing condition setting device is equipped on the control apparatus and then the radiographing apparatus is equipped with a transmission device that transmits results of discrimination of the discrimination device to the aforesaid control apparatus.

The embodiment of the invention employing CR (Computed Radiography) system will be described as follows, referring to the drawings.

First, the structure of the present embodiment will be described.

FIG. 1 is a conceptual diagram showing the overall structure of image radiographing system 100 in the present embodiment of the invention. As shown in FIG. 1, the image radiographing system 100 is composed of radiographing apparatus 10, reading apparatus 20, control apparatus 30, image output apparatus 40 and RIS/HIS 50, and each apparatus is connected through network N so that data can be transmitted and received.

Each apparatus constituting the image radiographing system 100 will be described as follows.

The radiographing apparatus 10 irradiates radiation on a breast of a patient as a subject to acquire a radiation image of the breast through radiographing. In the present embodiment, there will be described an example wherein a radiographing apparatus of a type to radiograph employing cassette C is applied.

Figure 2:
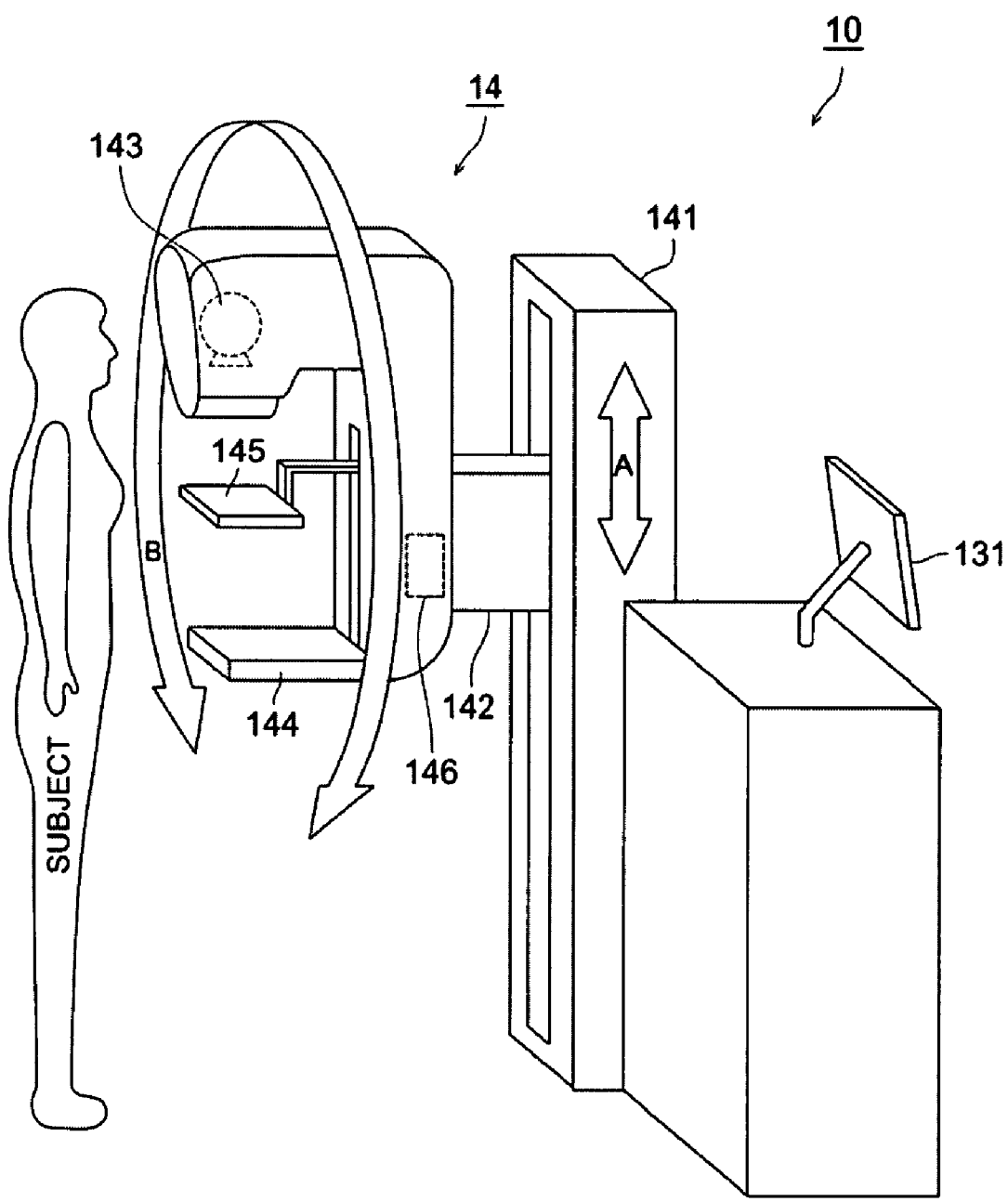
FIG. 2 is a structural diagram of appearance of radiographing apparatus 10.
Figure 3:
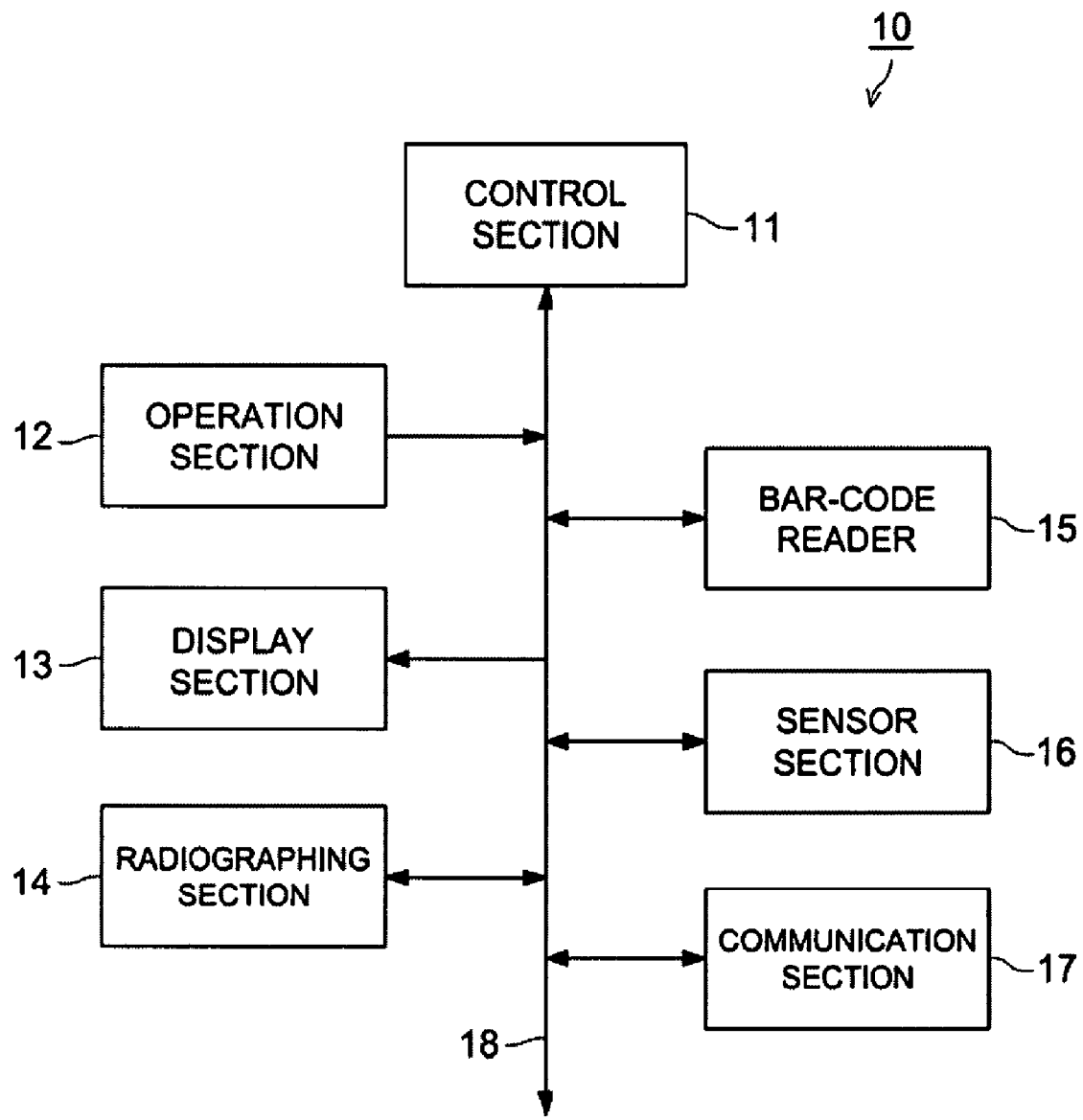
FIG. 3 is a block diagram showing a functional constitution of radiographing apparatus 10.

FIG. 2 shows an external structure of the radiographing apparatus 10, and FIG. 3 shows a functional structure of the radiographing apparatus 10. As shown in FIG. 3, the radiographing apparatus 10 is composed of control section 11, operation section 12, display section 13, radiographing section 14, bar-code reader 15, sensor section 16 and communication section 17, and respective sections are connected to each other through bus 18.

The control section 11 is composed of CPU (Central Processing Unit), RAM (Random Access Memory) and ROM (Read Only Memory). It reads various types of processing programs stored in ROM, and carries out various types of processing including processing on the radiographing apparatus 10 in breast image radiographing processing described later (see FIG. 9), in cooperation with the program which has been read out. For example, the control section 11 controls overall radiographing operations of respective sections of the radiographing apparatus 10 such as an automatic exposure control of radiation source 143 or control of rotation of radiographing section 14, for radiographing of a subject.

The operation section 12 is composed of various types of keys, such as numeral keys and function keys for inputting various types of setting conditions, and it outputs operation signals corresponding to the operated keys to the control section 11. Incidentally, the operation section 12 may also be composed of radiographing region keys for inputting information on the right and left showing a radiographing body part (left breast or right breast) and radiographing direction keys for instructing and inputting an angle of rotation of the radiographing section 14. With respect to these radiographing direction keys, keys corresponding to respective radiographing directions for vertical directions, directions for the inside and the outside and oblique directions, are prepared. When the key for directions for the inside and the outside is pressed, for example, the radiographing section 14 is rotated automatically at the rotating angle for radiographing in the directions for the inside and the outside. When the left breast region is designated in cooperation with the radiographing region key, for example, it is possible either to control the radiographing section 14 so that the direction of rotation may be made to be one direction (left direction) automatically or to constitute the control section 11 so that the direction of rotation and an angle of rotation may be set automatically based on the radiographing region and the radiographing direction included in radiographing order information.

As shown in FIG. 2, the display section 13 is composed of indication display 131 having therein LCD (Liquid Crystal Display), and it displays various types of display information such as input information coming from operation section 12 and results of processing by control section 11 on the indication display 131.

The radiographing section 14 radiographs a breast by irradiating radiation on the breast, and it is constructed to be capable of rising and lowering along columnar support 141 (to be capable of rising and Lowering in the direction shown with arrow A), as shown in FIG. 2, so that its height may be adjusted to the position of the breast of a patient. It is further constructed to be capable of rotating around its supporting shaft 142 (to be capable of rotating in the direction shown with arrow B) for changing the direction of radiographing. With respect to the rotation, it is either possible for an x-ray technician to rotate manually, or possible to operate operation section 12 to instruct the rotation.

Figure 4:
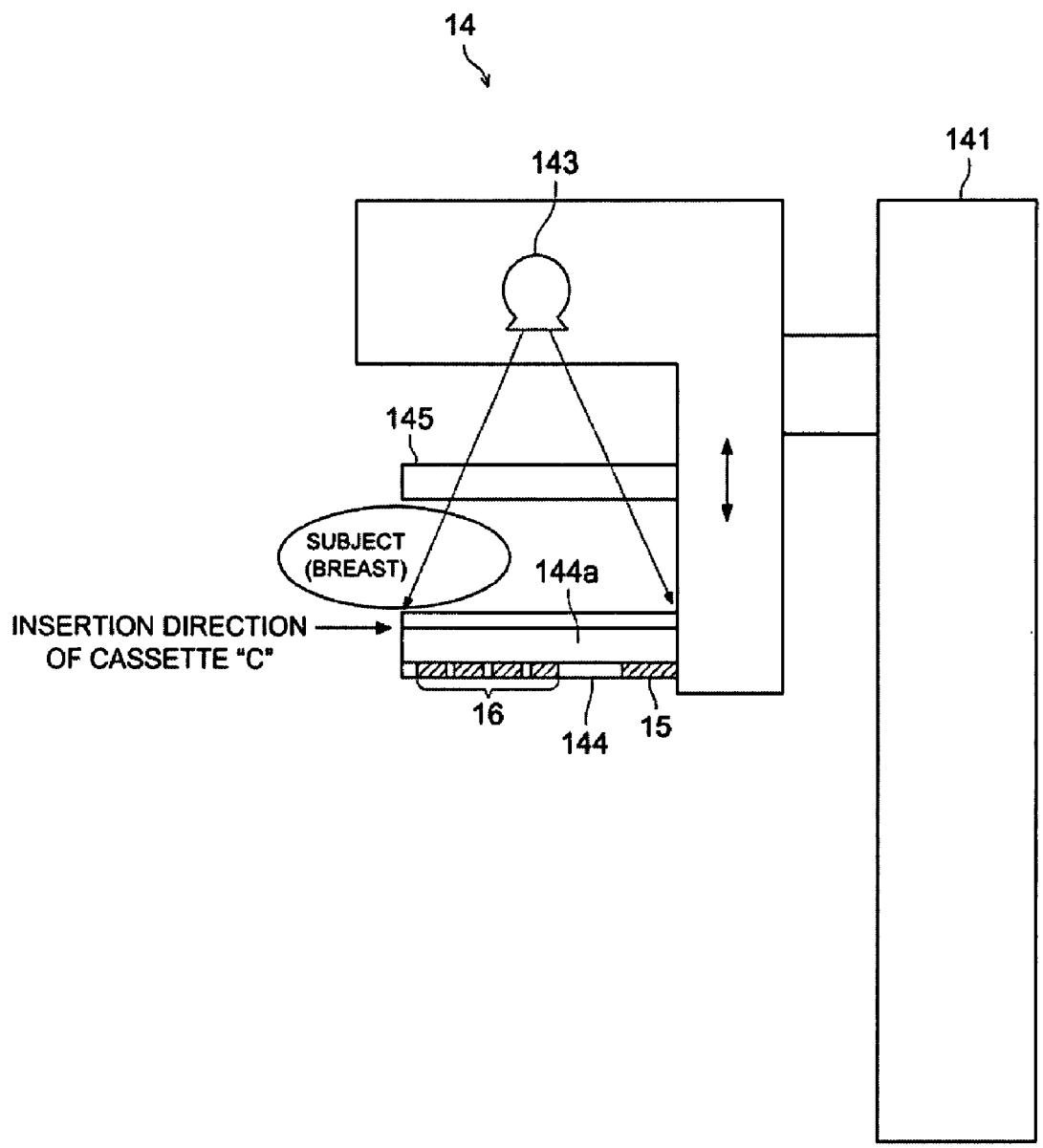
FIG. 4 is a side view of radiographing section 14.

On the radiographing section 14, there are arranged radiation source 143 irradiating radiation and radiographing table 144 on which a breast is placed facing each other, and pressure plate 145 for pressing a breast placed on the radiographing table 144 by nipping it is provided. FIG. 4 shows a side view of the radiographing section 14. As shown in FIG. 4, the radiographing section 14 is constructed so that cassette C can be mounted on cassette holder 144a of the radiographing table 144. The cassette C stores therein a stimulable phosphor plate and absorbs radiation transmitted through a subject, and radiation images are recorded on it. On the cassette C, there is provided a bar code that shows identification information (hereinafter referred to as cassette ID) for discriminating cassette C from others. On the other hand, on the radiographing table 144, there is provided bar-code reader 15 for reading a bar code displayed on cassette C. The bar code on cassette C is provided at the middle portion of one side on the back side of a recording surface for radiation images. Further, the bar-code reader 15 on the radiographing table 144 is provided at the middle portion of one side on the inner side in the direction of cassette insertion on the surface on which the back side of cassette C is mounted.

When mounting cassette C on the radiographing table 144, an x-ray technician can specify the direction of a subject recorded on cassette C to be one direction constantly, by inserting the cassette C so that one side having thereon a bar code may face a side of an insertion slot of cassette holder 144a, for example.

As shown in FIG. 2, inside the radiographing section 14, there is provided angle detecting section 146 that detects an angle by which the radiographing section 14 is rotated around supporting shaft 142 that represents an axis of rotation. The angle detecting section 146 outputs information of rotation angle detected in the course of radiographing to control section 11.

The bar-code reader 15 outputs cassette ID obtained by reading a bar code on the mounted cassette C to control section 11. Incidentally, an installation position for the bar-code reader 15 is not limited to the installation position shown in FIG. 4, provided that the installation position agrees with the bar code when cassette C is mounted on the radiographing table 144, and has no influence on radiographing of a subject.

Although the present embodiment has the system wherein cassette ID is read by the use of a bar code, it is also possible, without being limited to the foregoing, to employ a system wherein a radio IC tag that stores data of cassette ID is attached to cassette C, for example, and data of cassette ID stored in the radio IC tag are read out, or to employ other reading systems.

The sensor section 16 has plural detecting elements (hereinafter referred to as sensors) each detecting an amount of radiation transmitted through a breast and cassette C in the course of radiographing, and is provided under the cassette C mounted on cassette holder 144a as shown in FIG. 4. The sensor section 16 is composed, for example, of semiconductors. The control section 11 conducts automatic exposure control for irradiation of radiation of radiation source 143 based on the output value of each sensor of sensor section 16.

The communication section 17 is composed of communication interfaces such as a network interface card (hereinafter referred to as NIC) and modem, and conducts transmitting and receiving of data with control apparatus 30.

When information of an angle of rotation of radiographing section 14 is inputted from angle detecting section 146, the control section 11 distinguishes a radiographing region and a radiographing direction (hereinafter referred to as radiographing region and direction), based on the information of an angle of rotation.

Figure 5:
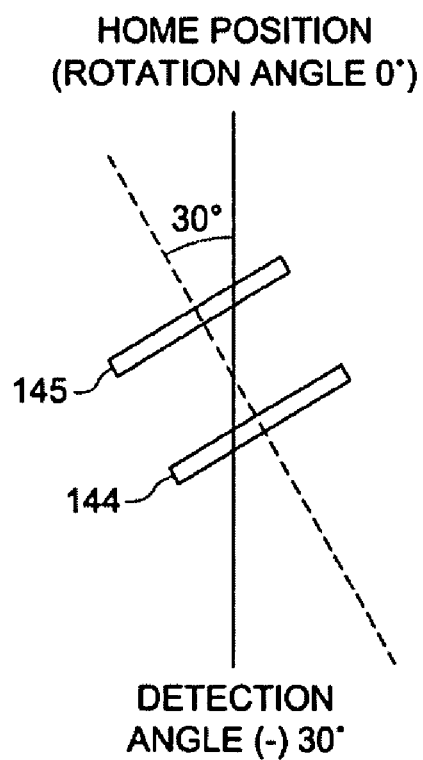
FIG. 5 is a diagram for illustrating an example of judgment for a direction of a region to be radiographed.
Figure 5:
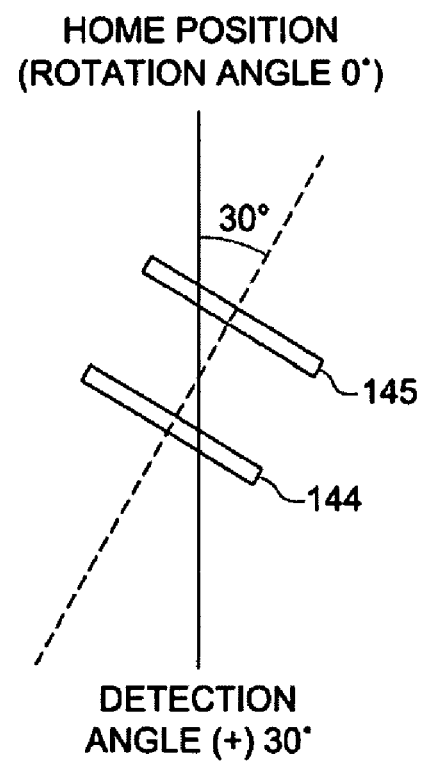

An example of distinction for the radiographing region and direction will be described as follows, referring to FIG. 5. Each of FIG. 5(a) and FIG. 5(b) is a diagram wherein pressure plate 145 and radiographing table 144 are viewed from the subject side. As shown in FIG. 5(a), if an angle of a home position where radiographing section 14 is not rotated is assumed to be 0°, an angle of rotation is detected to be "−30°" when the radiographing section is rotated by 30° counterclockwise from the position, for example, in order to radiograph the oblique direct-on of a left breast. Further, as shown in FIG. 5(b), when the radiographing section is rotated by 30° clockwise, for example, an angle of rotation is detected to be "+30°" in order to radiograph the oblique direction of a right breast. In other words, it is determined that the radiographing region is a left breast when the sign of the angle of rotation is "−", and that the radiographing region is a right breast when the sign of the detected angle of rotation is "+". Further, it is determined that the direction is in a vertical direction when the angle of rotation is in a range of 0-5° from the home position, the direction is in an oblique direction when the angle of rotation is in a range of 5-85°, and the direction is in an inside-outside direction when the angle of rotation is in a range of 85-90°.

The control section 11 makes to radiographing performance information that represents results of performance of radiographing in radiographing section 14 to be transmitted to control apparatus 30 through communication section 17. The radiographing performance information includes sensor data showing output values of respective sensors of sensor section 16 in the course of radiographing, values of tube voltage (unit; kV) in radiation source 143, tube current (unit; mA), pressure by pressure plate 145 (shown with a distance of movement of the pressure plate 145 (unit; mm), radiographing region and direction (shown with character code, radiographing region is shown by the first code, R represents a right breast and L represents a left breast, while, the next code shows a radiographing direction, CC represents a vertical direction, M represents an inside-outside direction, and MLO represents an oblique direction), and the radiographing performance information includes cassette ID of cassette C read by bar code reader 15 in the course of radiographing.

Figure 6:
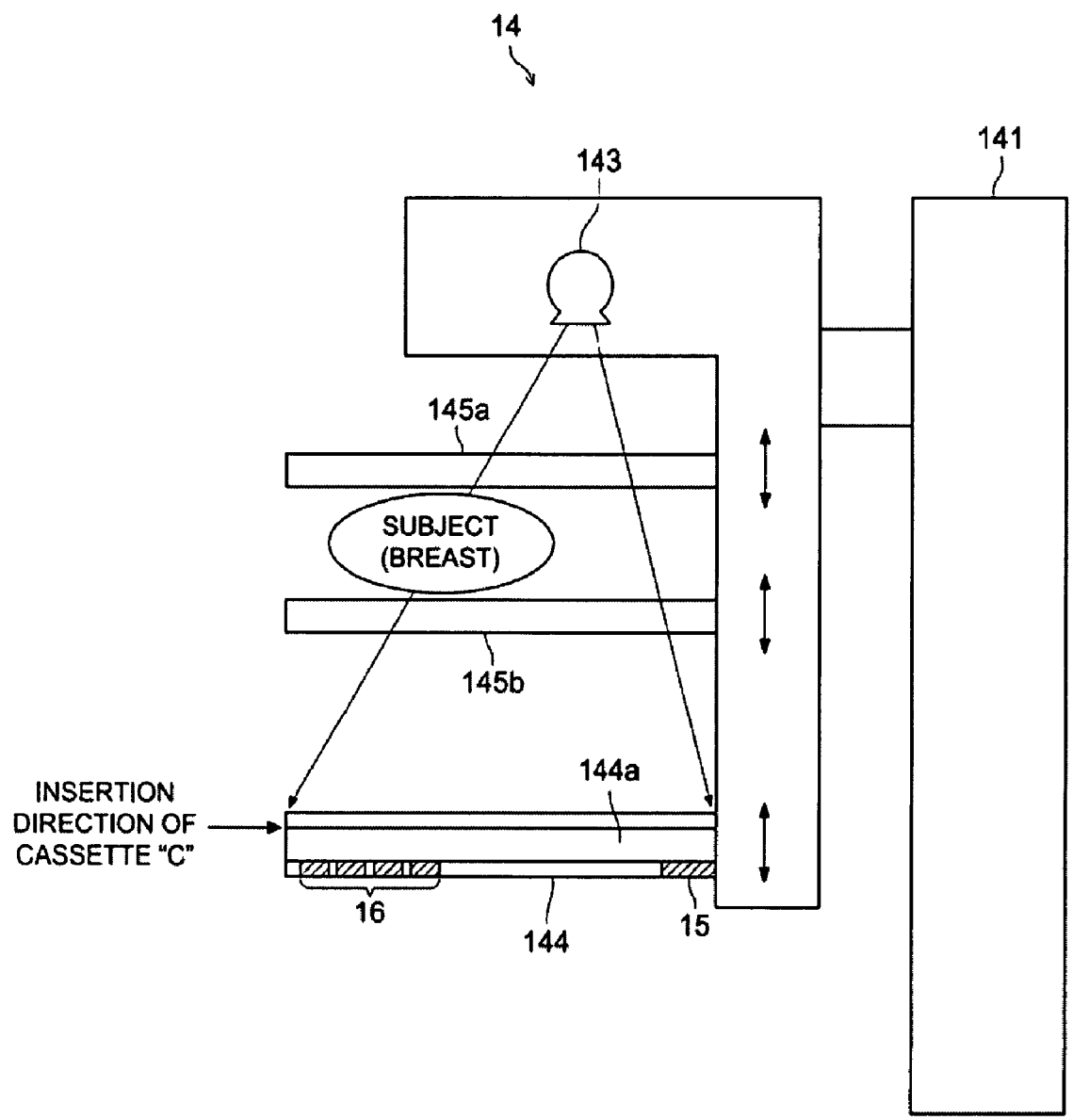
FIG. 6 is a side view of radiographing section 14 in the case of radiographing through phase contrast radiographing method.

When radiographing is conducted through a phase contrast radiographing method, radiographing section 14 of radiographing apparatus 10 is constructed as shown in FIG. 6. As shown in FIG. 6, two pressure plates 145a and 145b are provided on the radiographing section 14, and radiographing table 144 is arranged below them. These two pressure plates 145a and 145b and the radiographing table 144 are constructed to be capable of rising and lowering, and they can be adjusted in terms of height depending on a position of a subject. Further, in the case of phase contrast radiographing method, a size of cassette C used for radiographing is greater than that of an ordinary contact radiographing method, (a cassette size of 18 cm×24 cm is used in an ordinary contact radiographing method when a size of a subject is 18 cm×24 cm, but when radiographing magnification is 1.75 in the phase contrast radiographing method disclosed in Japanese Patent Publication Open to Public Inspection No. 2001-91479 and Japanese Patent Publication Open to Public Inspection No. 2001-311701, a size 14 inches×17 inches is used as a cassette size), and therefore, the radiographing table 144 is also formed to be enlarged in terms of its area.

Reading apparatus 20 shown in FIG. 1 is an apparatus that reads breast images recorded on cassette C and thereby to obtain digital image data. The reading apparatus 20 acquires image data of a breast image by irradiating exciting light onto a stimulable phosphor plate in the cassette C, applying photoelectric conversion to the stimulated light emitted from the plate and applying A/D conversion to the obtained image signal. The reading apparatus 20 is equipped with an unillustrated bar code reader to read cassette ID from bar code attached on cassette C, and transmits image data of breast image and cassette ID to the control apparatus 30 through an unillustrated interface by causing them to correlate to each other.

After receiving radiographing performance information including sensor data and cassette ID from radiographing apparatus 10 and receiving cassette ID and image data of breast images from reading apparatus 20, the control apparatus 30 causes the radiographing performance information and image data of breast images to correlate to each other, based on cassette ID, and establishes image processing conditions in image processing to be given to the image data, based on sensor data included in the radiographing performance information.

Figure 7:
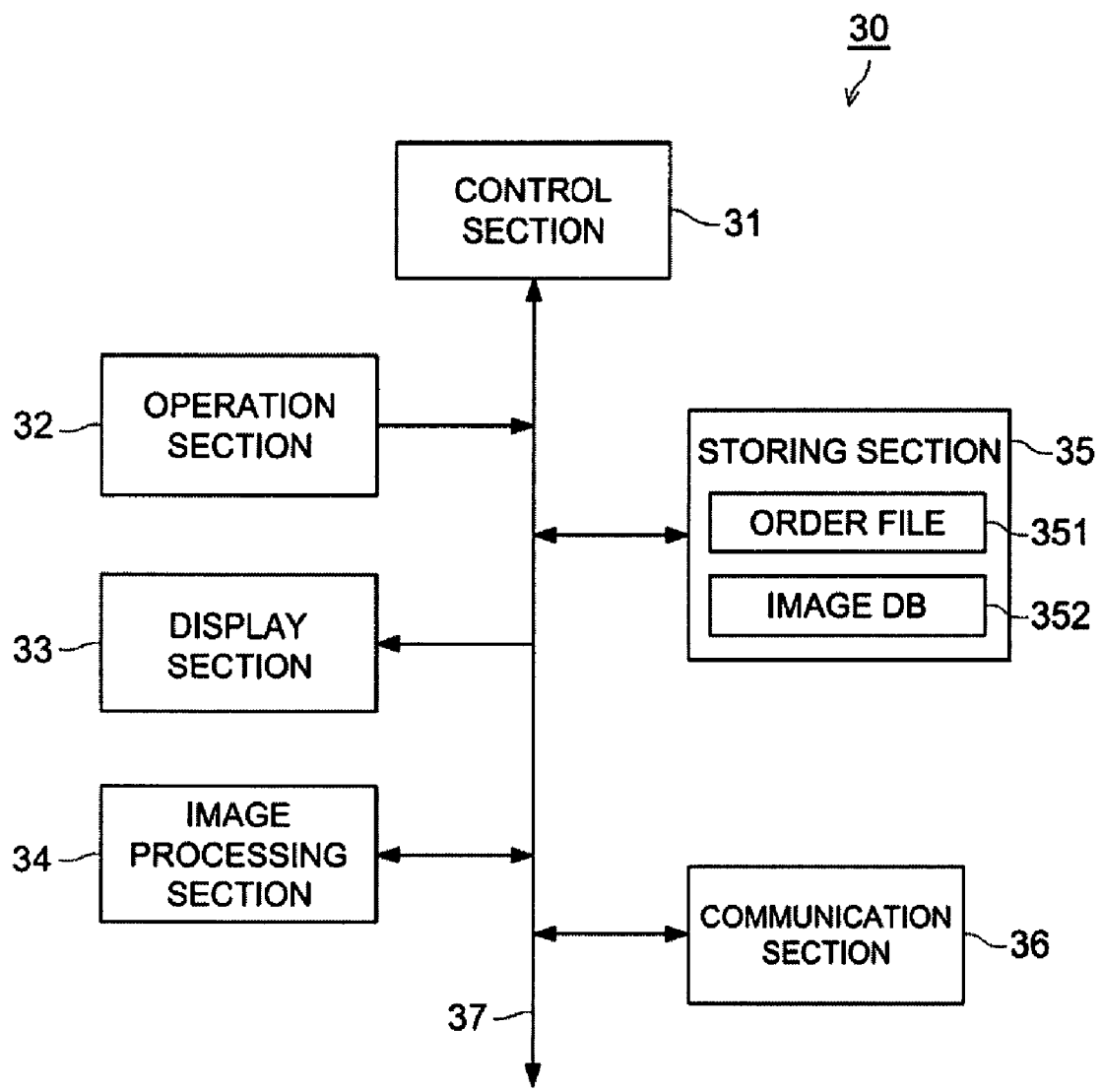
FIG. 7 is a block diagram showing a functional constitution of control apparatus 30.

FIG. 7 shows a functional structure of the control apparatus 30. As shown in FIG. 7, the control apparatus 30 is composed of control section 31, operation section 32, display section 33, image processing section 34, storing section 35 and communication section 36, and each section is connected to others through bus 37.

The control section 31 is composed of CPU, RAM and ROM, and reads out system programs and various types of processing programs stored in ROM, and carries out various types of processing including processing on the control apparatus 30 for a breast image radiographing processing (see FIG. 9) to be described later.

Operation section 32 is composed of a key board equipped with cursor keys, numeral input keys and various types of functional keys and of a pointing device such as a mouse, and outputs instruction signals inputted through key operations on key boards and through mouse operations to control section 31. Further, the operation section 32 may also be provided with a touch panel on a display screen of display section 33, and in this case, instruction signals inputted through the touch panel are outputted to the control section 31.

The display section 33 is composed of monitors such as LCD and CRT, and displays input instruction from operation section 32 and data, pursuantly to the instruction of display signals inputted from control section 31. For example, the display section 33 displays various types of operation screens and various types of display information such as breast images.

According to the instruction from control section 31, the image processing section 34 gives image data of breast images various types of image processing such as frequency emphasis processing to adjust image sharpness, gradation processing to adjust density and contrast and granularity control processing to control granularity, and generates images for diagnoses.

The storing section 35 is composed of a magnetic or an optical storing medium or of a semiconductor memory, to store data to be used for various types of processing conducted by control section 31 and data of results of processing conducted by control section 31.

The storing section 35 is equipped with order file 351 that stores radiographing order information 3510 in a way to be capable of updating the stored information. In the order file 351, radiographing order information 3510 are stored for each identification information 3511 (which is called order ID) for discriminating radiographing order information 3510 individually, as shown in FIG. 8. The radiographing order information 3510 includes information about a patient 3512 such as patient ID and a full name of the patient to be radiographed (hereinafter referred to as patient information) and information about radiographing 3513 such as a radiographing region and direction and a date of radiographing (hereinafter referred to as radiographing information). Further, cassette ID 3514 of cassette C used for radiographing of the radiographing order information and radiographing performance information 3515 are correlated to the radiographing order information.

Further, in the storing section 35, a mammary gland content rate and an output value of a sensor of sensor section 16 in the case of irradiating radiation on a breast having each of the mammary gland content rate are stored in advance, so that they may be corresponding to each other. These are data obtained by measuring in advance by the use of a phantom for experiments for a breast with each mammary gland content rate. The mammary gland content rate is in a range of 0-100 wherein 0 corresponds to fat (no mammary gland), and a larger value represents a higher degree of density of mammary gland.

The communication section 36 is equipped with a communication interface such as a NIC and a modem, and conducts transmitting and receiving of data between itself and radiographing apparatus 10, reading apparatus 20, image output apparatus 40 or RIS/HIS 50. For example, it receives radiographing order information from RIS/HIS 50 before radiographing, then, receives radiographing performance information from radiographing apparatus 10 after radiographing, and receives, from reading apparatus 20, image data of breast images and cassette ID corresponding to the image data of breast images.

When cassette ID corresponding to radiographing order information is inputted through operation section 32 before radiographing, control section 31 causes order file 351 to store the cassette ID 3514 by correlating the cassette ID 3514 to the radiographing order information 3510. This is called cassette registration. Then, when radiographing performance information 3515 is received from radiographing apparatus 10 after radiographing, control section 31 causes order file 351 to store the radiographing performance information 3515 by correlating the radiographing performance information 3515 to the radiographing order information 3510, based on cassette ID 3514 included in the received radiographing performance information and on cassette ID 3514 corresponding to the radiographing order information 3510. Further, when image data of breast images and cassette ID 3514 corresponding to the image data of breast images are received from reading apparatus 20, control section 31 causes image DB 352 to store the image data by correlating the image data of breast images to radiographing order information 3510 and radiographing performance information 3515 based on the cassette ID 3514. This is called image registration.

The control section 31 discriminates a type of the radiographed breast based on the sensor data included in radiographing performance information transmitted from radiographing apparatus 10, namely, on the output value obtained from each sensor of sensor section 16. Specifically, the control section 31 acquires a mammary gland content rate corresponding to an output value obtained from each sensor of sensor section 16, namely, a mammary gland content rate of a breast portion corresponding to a position of each sensor, by referring to prior measurement data of each mammary gland content rate stored in storing section 35 in advance. Further, control section 31 calculates an average mammary gland content rate of an overall breast area by calculating an average of mammary gland content rate of breast portion on each sensor. Thus, a type of a breast is discriminated, based on the average mammary gland content rate and on the state of distribution of mammary gland content rate. Namely, a discrimination device is realized by the control section 31.

The control section 31 establishes image processing conditions on image processing section 34 based on the results of the discrimination of the breast type. Namely, an image processing condition setting device is realized by the control section 31.

The image output apparatus 40 is an apparatus that records and outputs images on a recording medium such as a film based on image data inputted from control apparatus 30.

RIS/HIS 50 is a system that controls information in a department of radiology or in a hospital panoptically. In the RIS/HIS 50, an inspection request sent by a doctor is accepted, and radiographing order information is generated. Then, the generated radiographing order information is transmitted to control apparatus 30 through network N.

Next, operations in the present embodiment will be described.

Figure 9:
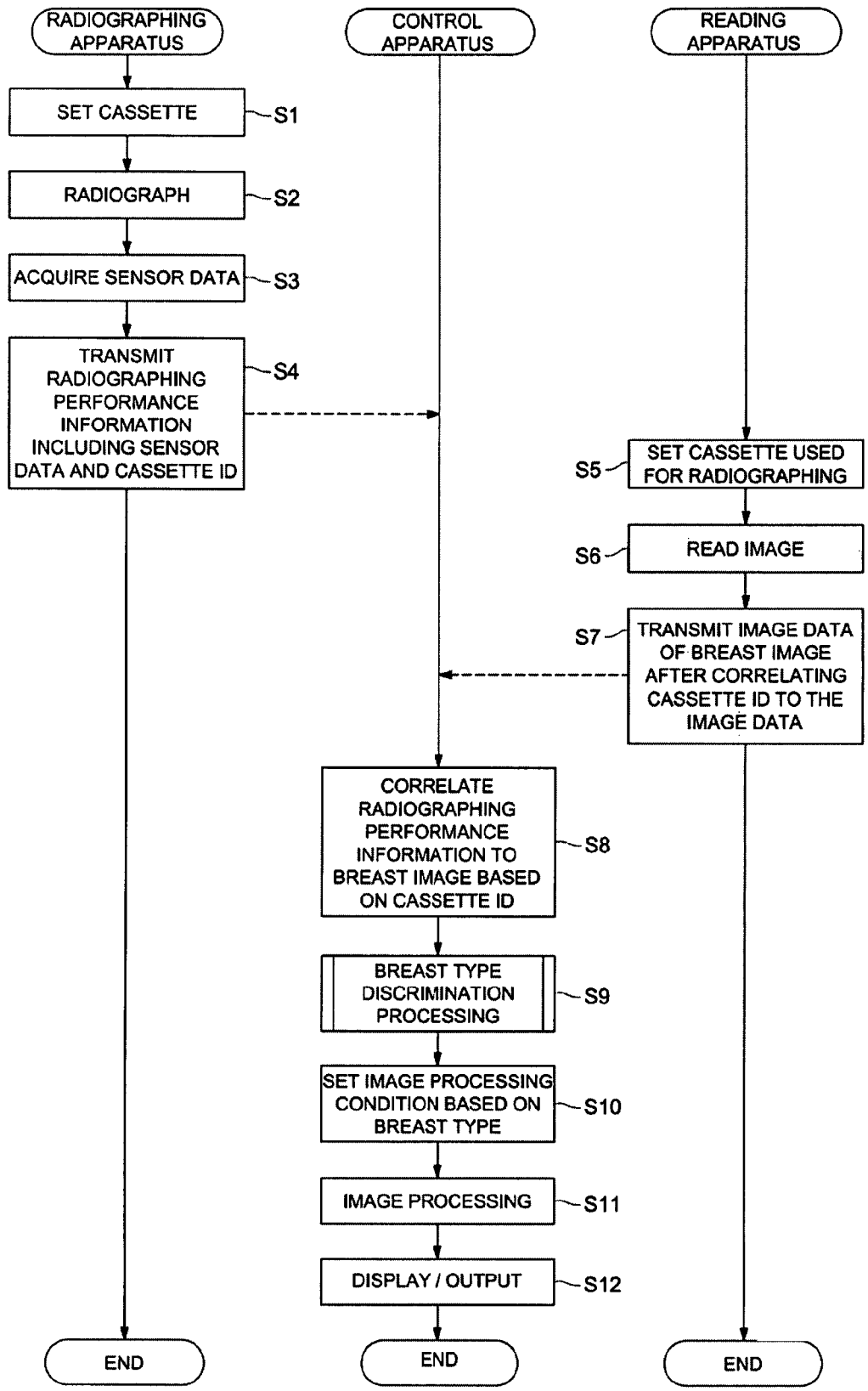
FIG. 9 is a flow chart showing breast image radiographing processing practiced in image radiographing system 100.

FIG. 9 is a flow chart showing breast image radiographing processing practiced in image radiographing system 100.

First, in radiographing apparatus 10, cassette C is loaded on radiographing table 144 according to operations by an x-ray technician to insert a cassette into the cassette insertion slot (step S1). In the radiographing apparatus 10, when cassette C is loaded in the correct direction, namely, when cassette C is loaded so that bar code reader 15 and a bar code may face each other, the bar code is read by the bar code reader 15, and acquisition of cassette ID is carried out. When the cassette C is not loaded in the correct direction, and the bar code is not read accordingly, an error message notifying erroneous loading is displayed on display section 13.

Next, radiographing conditions are set through operational input by an x-ray technician from operation section 12. Incidentally, the radiographing conditions may also be arranged to be set automatically based on information of radiographing region and radiographing direction included in the radiographing order information registered in advance, based on information of "left oblique" shown, for example, in FIG. 8, and on the past radiographing conditions for the same subject. Further, an x-ray technician conducts positioning for radiographing, arrangement of a breast representing a subject on radiographing table 144, rotation of radiographing section 14 and pressing to a breast with vertical movements of pressure plate 145.

Next, when an instruction for radiographing is inputted from operation section 12, a radiation is irradiated from radiation source 143 through control of control section 11, and radiographing is carried out (step S2). After the radiographing is started, an amount of radiation transmitted through a subject is detected by each sensor of sensor section 16, and an output value of each sensor is outputted to control section 11. Then, when the output value from each sensor arrives at an amount of radiation established in advance, irradiation of radiation from radiation source 143 is stopped by control section 11.

In radiographing by radiation, if an amount of radiation irradiated on a subject is not sufficient, graininess of images (granular appearance) is worsened, and excellent images suitable for diagnoses are not obtained. On the other hand, if an amount of radiation is too much, a radiation exposure to a subject is increased, which is not preferable. Therefore, in control section 11 of radiographing apparatus 10, an automatic exposure control for controlling an amount of radiation is conducted based on an output value from each sensor of sensor section 16.

After the radiographing, the control section 11 acquires output values (sensor data) in each sensor of sensor section 16 (step S3) and transmits radiographing performance information including sensor data and cassette ID to control apparatus 30 through communication section 17 (step S4).

After the radiographing is terminated, exposed cassette C is loaded on reading apparatus 20, by means of cassette insertion operations by an x-ray technician (step S5). On the reading apparatus 20, cassette ID is read by a bar code reader, if cassette C is loaded in the correct direction. When cassette C is loaded in the correct direction, breast images recorded on the loaded cassette C is read by the reading apparatus 20 (step S6), and image data of breast images obtained and cassette ID thus read are caused to correspond to each other to be transmitted to control apparatus 30 (step S7).

In the control apparatus 30, when radiographing performance information 3515 including sensor data and cassette ID 3514 is received from radiographing apparatus 10 through communication section 36, and when image data of breast images corresponding to cassette ID 3514 are further received from reading apparatus 20, radiographing performance information 3515 with which the cassette ID 3514 agrees and the image data of breast images are caused to correspond to each other by control section 31 (step S8). Specifically, by control section 31, the radiographing performance information 3515 is caused to correspond to radiographing order information 3510 to be stored in order file 351, based on cassette ID 3514 included in the radiographing performance information 3515 and on cassette ID 3514 corresponding to the radiographing order information 3510. Further, image data of breast images received are stored in image DB 352 by control section 31, and the image data, the radiographing order information 3510 and radiographing performance information 3515 are caused to correspond to each other, based on the cassette ID 3514 corresponding to image data and on the cassette ID corresponding to the radiographing order information 3510. The radiographing order information 3510 and radiographing performance information 3515 both corresponding to the image data are written in a header portion of the image data as information incidental to the image data.

Next, discrimination processing for a type of a breast is conducted by control section 31 (step S9).

Discrimination processing for a type of a breast will be described as follows, referring to FIG. 10.

Figure 10:
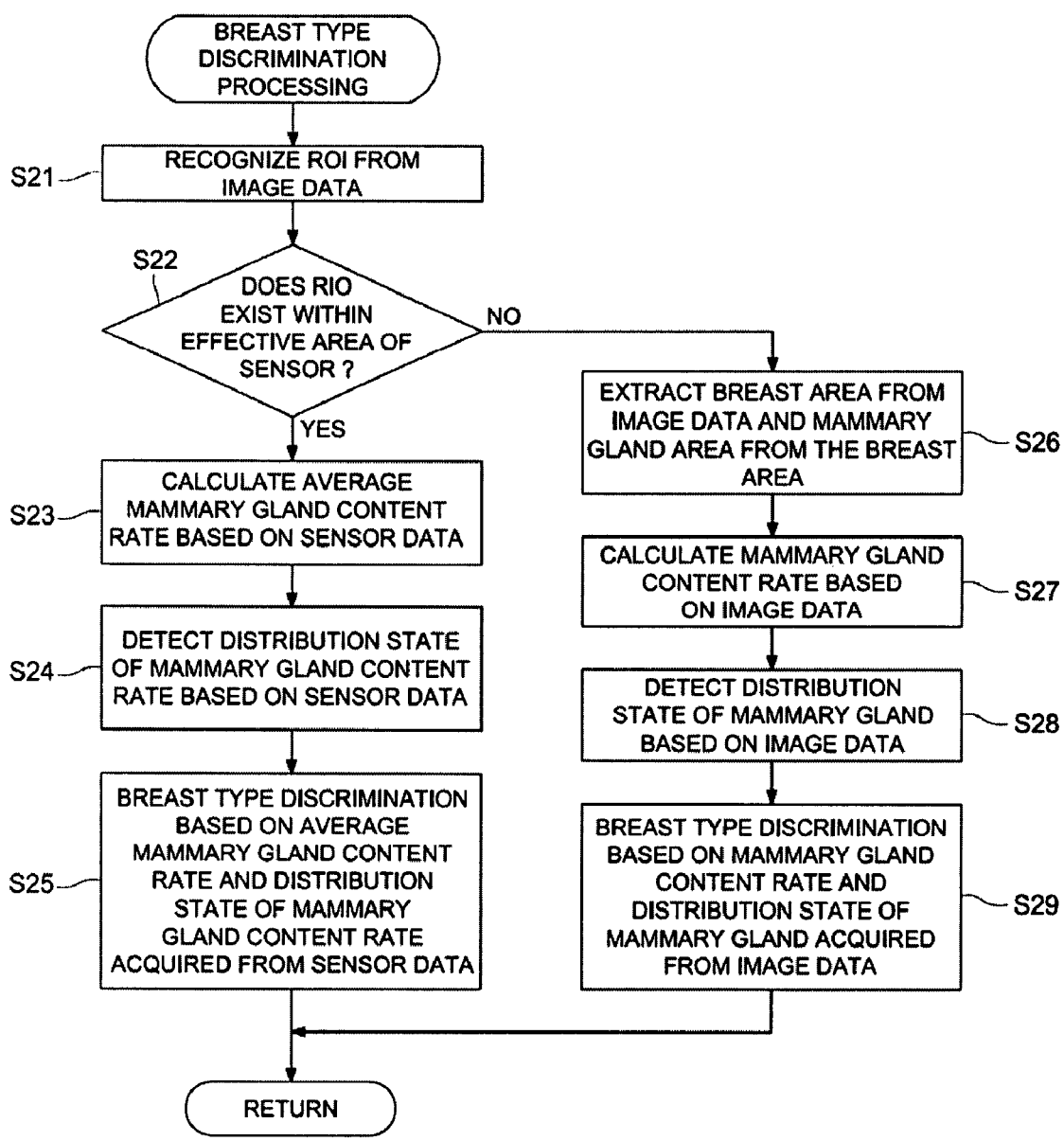
FIG. 10 is a flow chart showing the processing of breast type discrimination.

As shown in FIG. 10, a region to be paid attention for diagnosis (ROI) is recognized by control section 31 from image data of breast images (step S21). For example, a high density mammary gland area in the breast area is recognized as ROI.

Next, control section 31 judges whether the recognized ROI is within an effective area of respective sensors of sensor section 16 of radiographing apparatus 10 or not (step S22).

Whether the ROI is included or not in the effective area of sensors is judged from whether a direct radiation irradiation area (an area of radiation which does not pass through a subject) exists or not in the tip side of the breast. In other words, it is judged from the number and the positions of sensors which have large output (larger compared to a radiation transmitting area of the subject).

FIG. 11(a) shows an example wherein ROI 62 is within the effective area of sensors. In FIG. 11(a), the whole of breast area M including ROI 62 in high density mammary gland area 63 is within effective area 61 of the sensor. FIG. 11(b), on the other hand, is an example wherein ROI 62 is not within the effective area 61 of the sensor. In FIG. 11(b), high density mammary gland area 63 including ROI 62 is out of the effective area 61 of the sensor, because breast area M is large.

When ROI is within the effective area of the sensor (step S22; YES), a mammary gland content rate corresponding to an output value of each sensor is acquired from storing section 35 by control section 31 based on sensor data from each sensor, and an average mammary gland content rate representing an average of mammary gland content rates in respective sensor positions is calculated (step S23).

Next, control section 31 detects the state of distribution of mammary gland content rate based on sensor data coming from each sensor (step S24).

Then, based on the average mammary gland content rate and the state of distribution of average mammary gland content rates obtained from the sensor data (2-dimensional distribution as shown in FIGS. 12(a)-12(c)), a type of a breast is discriminated (step S25), and the flow moves to Step S10 in FIG. 9. Here, FIGS. 12(a)-12(c) show the cases where ROI exists in the effective area of sensors as shown in FIG. 11 and are enlarged schematic diagrams illustrating sensor output patterns around ROI.

A discrimination method for the breast type based on the average mammary gland content rate and on the state of distribution of mammary gland content rates will be described, referring to FIGS. 12(a), 12(b) and 12(c). Each of numerical values shown in FIGS. 12(a), 12(b) and 12(c) shows a mammary gland content rate of a breast portion calculated in the step S23 at the position corresponding to each sensor. As shown in FIG. 12(a), when an average mammary gland content rate is high (80% or more for example) and a distribution of mammary gland is broad, it is discriminated to be a high density type. As shown in FIG. 12(b), when an average mammary gland content rate is low (30% or less for example) and a distribution of mammary gland is narrow, it is discriminated to be a fatty type. Further, as shown in FIG. 12(c), in the case of other occasions, it is discriminated to be other types. The mammary gland distribution being large means that there are many sensors whose signals of calculated mammary gland content are large (spreading in a large area).

When ROI is not within an effective area of the sensor in step S22 (step S22; NO), a breast area is extracted from image data and a mammary gland area is extracted from the breast area by control section 31 (step S26), because discrimination of a breast type based on sensor data is difficult.

The breast area can be recognized through methods, for example, to obtain a histogram of signal values of all pixels of image data, then, to determine a threshold value by a method of discrimination analysis and to conduct binarization for the whole image data by using the determined threshold value. The mammary gland area can be recognized through methods, for example, to establish a local area in images, then, to determine a threshold value based on a signal value of a pixel in the local area and to conduct binarization for to the breast area by using the determined threshold value (Japanese Patent Publication Open to Public Inspection No. 2001-238868).

Next, a rate of the number of pixels of the mammary gland area with respect to the number of pixels of the breast area is calculated by control section 31 as an amount of characteristic indicating a mammary gland content rate in the breast area (step S27). Then, dispersion of image signal values in the mammary gland area is calculated by control section 31 to be detected as an amount of characteristic indicating a state of distribution of mammary glands (step S28).

Then, based on the rate of the number of pixels which is an amount of characteristic indicating the mammary gland content rate and the dispersion value which is an amount of characteristic indicating the state of distribution of mammary glands both obtained from image data, a breast type is discriminated (step S29) and the flow moves to step S10 in FIG. 9. For example, if the mammary gland content rate (the rate of the number of pixels) is in a range of 90%-100% and mammary glands are distributed in a broad range (the dispersion value as an amount of characteristic is in a range of small to medium), a breast type is discriminated to be a high density type. If the mammary gland content rate is in a range of 1%-20% and distribution range of mammary glands is narrow (the dispersion value as an amount of characteristic is in a range of medium to large), mammary gland tissues hardly exist in the mammary gland area, and a breast type is discriminated as a fatty type. If the mammary gland content rate is in a range of 20-90% which is a medium degree between both types, mammary gland tissues are discriminated to be scattered on a part of the breast area (the dispersion value as an amount of characteristic is large), the breast type is classified to be a heterogeneous high density type or a mammary gland scattering type.

Next, image processing conditions are established by control section 31, based on the breast type discriminated in the breast type discrimination processing (step S10).

In control apparatus 30, frequency emphasizing processing to adjust image sharpness and gradation processing to adjust density and contrast are given by image processing section 34 to image data of breast images inputted. An example of the frequency emphasizing processing includes one wherein a prescribed spatial frequency components are emphasized by generating a non-sharpness image by means of extraction of only low frequency components of image signals of an original image, and by adding the non-sharpness image deducted from image signals of original images and multiplied by an emphasis coefficient (hereinafter referred to as emphasis degree) established in advance to the original image signals.

An example of a method of setting image processing conditions according to a breast type will be described as follows, referring to FIG. 13. FIG. 13 shows image processing conditions set corresponding to each breast type and examples of images. In this case, there will be described an occasion wherein γ value in contrast adjustment processing and an emphasis degree in frequency emphasizing processing are established as image processing conditions. The γ value in contrast adjustment processing corresponds to an inclination of a curved line showing an output value with respect to the input value, which shows that the greater the γ value is, the higher the contrast is. Further, the emphasis degree in the frequency emphasizing processing in this case is determined to be in five ranks (1-5) depending on strength and weakness of frequency emphasis, which shows that the greater the numerical value is, the stronger the frequency emphasis processing is, while, the smaller the numerical value is, the weaker the frequency emphasis processing is, making rank 3 as the basis.

As shown in FIG. 13(a), when a breast type is a high density type, γ value in the contrast adjustment processing is set to 3.0, and the emphasis degree in the frequency emphasizing processing is set to 4. As shown in FIG. 13(b), when a breast type is a fatty type, γ value in the contrast adjustment processing is set to 5.0, and the emphasis degree in the frequency emphasizing processing is set to 4. As shown in FIG. 13(c), when a breast type is another type, γ value in the contrast adjustment processing is set to 4.0, and the emphasis degree in the frequency emphasizing processing is set to 3.

After image processing conditions are established, image processing such as contrast adjustment processing and frequency emphasis processing based on the established image processing conditions are given by image processing section 34, and images for diagnoses are generated (step S11). Then, breast images are displayed by control section 31 on display section 33 based on image data which have been subjected to image processing, and image data which have been subjected to image processing are outputted to image output apparatus 40 through communication section 36 (step S12). On the image output apparatus 40, breast images are recorded on a recording medium such as a film to be outputted.

Thus, breast image radiographing processing is terminated.

As described above, when ROI (high density mammary gland area or the like) is within an effective area of respective sensors of sensor section 16, a mammary gland content rate is acquired based on sensor data, a breast type is discriminated based on the average mammary gland content rate and on the state of distribution of mammary gland content rates, and image processing conditions are set based on the results of the discrimination. Therefore, even when a subject is a tissue structure having a large individual difference, stable image processing results can be obtained. In the meantime, a type of the breast is not limited to the aforesaid examples.

Further, even when ROI is not within an effective area of respective sensors of sensor section 16, image processing conditions can be established based on image data, thus, it is not necessary to conduct re-radiographing caused by positioning failure, which makes it possible to reduce the number of radiation exposures for a patient caused by re-radiographing. As an example where ROI is not within an effective area of respective sensors of sensor section 16, there are given a large breast, positioning failure in the case of enlarged radiographing and an erroneous setting of a sensor.

Since the discrimination of a breast type and the setting of image processing conditions are conducted on the control apparatus 30 side, existing radiographing apparatus 10 can be used as it is.

Incidentally, contents of the description in the aforesaid embodiment are examples of an image radiographing system relating to the invention, to which the invention is not limited. Detailed structures and detailed operations of each apparatus constituting the system may be modified without departing from the spirit and scope of the invention.

For example, in the aforesaid embodiment, the discrimination of a breast type is conducted after radiographing performance information is acquired from radiographing apparatus 10 and image data are acquired from reading apparatus 20, both by control apparatus 30. However, when conducting discrimination of a breast type based on sensor data, it is also possible to conduct discrimination of a breast type after radiographing performance information is acquired from radiographing apparatus 10 and before image data are acquired from reading apparatus 20. In an actual radiographing job site, an x-ray technician moves from the spot where radiographing apparatus 10 is installed to the spot where reading apparatus 20 is installed so that the reading apparatus 20 may read cassette C. If the discrimination of a breast type can be completed in control apparatus 30 during the period of this movement of the x-ray technician and of the processing of image reading by the reading apparatus 20, it is possible to give proper image processing immediately after acquiring image data from the reading apparatus 20. Therefore, it is possible to provide images for diagnoses promptly without affecting a job flow of an x-ray technician and others.

Though the radiographing apparatus 10, the reading apparatus 20 and the control apparatus 30 are described as separate items in the aforesaid embodiment, an apparatus wherein functions of the aforesaid items are combined may also be employed. It is further possible to employ a structure wherein an image radiographing system 100 is equipped with a plurality of radiographing apparatuses 10 or with a plurality of reading apparatuses 20.

In the aforesaid embodiment, an explanation was given with an example of the image radiographing system wherein cassette C housing therein a stimulable phosphor plate is used, and radiographed cassette C is read by reading apparatus 20, and then image data of breast images thus obtained are outputted to control apparatus 30. However, it is also possible to employ a structure wherein FPD (Flat Panel Detector) equipped with an automatic exposure control device is used as a radiographing device, and radiographing order information (patient information or the like), image data generated by FPD and radiographing performance information (sensor data, radiographing region and direction and others) are transmitted to the control apparatus 30 from the FPD.

Though sensor data are transmitted from radiographing apparatus 10 to control apparatus 30 to discriminate a breast type in the control apparatus 30 in the aforesaid embodiment, it is also possible to discriminate a breast type in radiographing apparatus 10, and to transmit radiographing performance information including the discriminated breast type to the control apparatus 30. In this case, a load of processing in the control apparatus 30 is reduced, because a type of a breast is discriminated on the radiographing apparatus 10 side. In addition, when FPD is used as a radiographing apparatus, it is preferable to preserve image data and results of discrimination of a breast type in a memory stored in FPD by causing them to correspond to each other for each radiographing, and to transmit them collectively to the control apparatus 30 after completion of all radiographing operations, thus, it is possible to control a load of communication in the network and to avoid network busy.

Further, when conducting ordinary four radiographing operations (oblique direction of a left breast, oblique direction of a right breast, vertical direction of a left breast and vertical direction of a right breast) for the same patient, it is either possible to conduct discrimination of a breast type for the first radiographing, and thereby to use the same discrimination result for each of remaining three radiographing operations, or possible to use the discrimination result for the first left breast (right breast) as a discrimination result for the left breast (right breast) thereafter. In this case, a time period for discrimination results can be shortened.

In the invention, a type of a breast is discriminated based on output values of plural detecting elements, and image processing conditions are set based on the results of the discriminations, whereby, even when a subject is a tissue structure having a large individual difference, stable image processing results can be obtained.

In the invention, stable image processing results can be obtained, because a type of a breast is discriminated based on a mammary gland content rate and on the state of distribution of the mammary gland content rates.

In the invention, an existing radiographing apparatus can be used as it is, because discrimination of a type of a breast and establishment of image processing conditions are conducted on the control apparatus side.

In the invention, a load of processing in the control apparatus is reduced, because discrimination of a type of a breast is conducted on the radiographing apparatus side.

What is claimed is:

1. An image radiographing system comprising:
a cassette for acquiring a breast image; and
a radiographing apparatus including:
a radiographing device having a radiation source for radiographing a breast so as to acquire a breast image in the cassette by detecting a radiation which has been emitted from the radiation source and has been transmitted through the breast;

a detection device having a plurality of detection elements for detecting a dose of the radiation having passed through the breast during radiographing; and a control device for controlling the radiation source based on output values of the plurality of detection elements, the image radiographing system further comprising:

a reading apparatus for reading the breast image;

a control apparatus for generating an image for diagnosis by applying image processing to a radiation image data which has been generated by reading the acquired breast image by the reading apparatus;

a discrimination device for discriminating a type of the radiographed breast based on the output vales of the plurality of detection elements; and an image processing condition setting device for setting an image processing condition of the image processing based on a discrimination result of the discrimination device.

2. The image radiographing system of claim 1, wherein the discrimination device acquires a mammary gland content rate of the breast at a position corresponding to a position of each of the plurality of detection elements based on the output values of the plurality of detection elements, and discriminates the type of the radiographed breast based on the mammary gland content rate and a state of distribution of the mammary gland content rate.

3. The image radiographing system of claim 1, wherein the radiographing apparatus comprises a transmission device for transmitting the output values of the plurality of detection elements to the control apparatus and the discrimination device and the image processing condition setting device are provided to the control apparatus.

4. The image radiographing system of claim 1, wherein the discrimination device is provided to the radiographing apparatus and the image processing condition setting device is provided to the control apparatus and the radiographing apparatus comprises a transmission device for transmitting a discrimination result of the discrimination device to the control apparatus.

5. The image radiographing system of claim 1, wherein the radiographing device comprises a cassette holder and detects the radiation by the cassette mounted on the cassette holder and the radiation image data is generated by mounting the cassette on the reading apparatus.

6. The image radiographing system of claim 5, wherein the detection device is located adjacent to the cassette holder and on an opposite side of the cassette holder with respect to the radiation source.

7. The image radiographing system of claim 5, wherein the cassette holder comprises a cassette ID reading device for reading a cassette ID of the cassette.

8. The image radiographing system of claim 1, wherein the control device distinguishes a radiographing region and a radiographing direction by an angle of rotation of the radiographing device.

9. The image radiographing system of claim 1, further comprising:

a storing section which stores correspondence between a mammary gland content rate and an output value of a detection element.

10. The image radiographing system of claim 1, wherein the discrimination device discriminates based on a state of distribution of mammary gland.

11. The image radiographing system of claim 1, wherein when a ROI is within an effective area, the discrimination device discriminates based on an average mammary gland content rate and a state of distribution of mammary gland content rate and when the ROI is not within an effective area, the discrimination device discriminates based on a mammary gland content rate and a state of distribution of mammary gland.

12. An image radiographing system which generates a radiation image of a breast by using a radiation emitted by a radiation source, the image radiographing system comprising:

a radiographing apparatus including:

a radiographing device for radiographing a breast so as to acquire a radiation image data of the breast by detecting a radiation which has been emitted from the radiation source and has been transmitted through the breast;

a detection device having a plurality of detection elements for detecting a dose of the radiation having passed through the breast during radiographing; and a control device for controlling the radiation source based on output values of the plurality of detection elements;

a first transmission device for transmitting a control signal from the control device for a control of the radiation source, the image radiographing system further comprising:

a control apparatus for generating an image for diagnosis by applying image processing to the acquired radiation image data of the breast;

a discrimination device for discriminating a type of the radiographed breast based on the output vales of the plurality of detection elements; and an image processing condition setting device for setting an image processing condition of the image processing based on a discrimination result of the discrimination device.

13. The image radiographing system of claim 12, wherein the radiographing apparatus is a FPD.

14. The image radiographing system of claim 12, wherein the discrimination device acquires a mammary gland content rate of the breast at a position corresponding to a position of each of the plurality of detection elements based on the output values of the plurality of detection elements, and discriminates the type of the radiographed breast based on the mammary gland content rate and a state of distribution of the mammary gland content rate.

15. The image radiographing system of claim 12, wherein the radiographing apparatus comprises a second transmission device for transmitting the output values of the plurality of detection elements to the control apparatus and the discrimination device and the image processing condition setting device are provided to the control apparatus.

16. The image radiographing system of claim 12, wherein the discrimination device is provided to the radiographing apparatus and the image processing condition setting device is provided to the control apparatus and the radiographing apparatus comprises a second transmission device for transmitting a discrimination result of the discrimination device to the control apparatus.

17. The image radiographing system of claim 12, further comprising:

a storing section which stores correspondence between a mammary gland content rate and an output value of a detection element.

18. The image radiographing system of claim 12, wherein the discrimination device discriminates based on a state of distribution of mammary gland.

19. The image radiographing system of claim 12, wherein when a ROI is within an effective area, the discrimination device discriminates based on an average mammary gland content rate and a state of distribution of mammary gland content rate and when the ROI is not within an effective area, the discrimination device discriminates based on a mammary gland content rate and a state of distribution of mammary gland.

* * * * *